United States Patent [19]

Deinhammer

[11] 4,440,959
[45] Apr. 3, 1984

[54] PROCESS FOR THE MANUFACTURE OF CHLOROACETALDEHYDE DIMETHYL ACETAL

[75] Inventor: Wolfgang Deinhammer, Burghausen, Fed. Rep. of Germany

[73] Assignee: Wacker-Chemie GmbH, Munich, Fed. Rep. of Germany

[21] Appl. No.: 437,909

[22] Filed: Nov. 1, 1982

[30] Foreign Application Priority Data

Dec. 15, 1981 [DE] Fed. Rep. of Germany ....... 3149652

[51] Int. Cl.$^3$ .................. C07C 41/48; C07C 41/58
[52] U.S. Cl. ................................................ 568/604
[58] Field of Search ........................................ 568/604

[56] References Cited

U.S. PATENT DOCUMENTS 2,330,570 9/1943 Filachione .................. 568/604
2,411,826 11/1946 Filachione .................. 568/604
4,130,592 12/1978 Vogt et al. .................. 568/604

OTHER PUBLICATIONS

Filachione, J.A.C.S. 61 (1939) pp. 1705–1706.

*Primary Examiner*—Howard T. Mars
*Attorney, Agent, or Firm*—Collard, Roe & Galgano

[57] ABSTRACT

The invention relates to an improved process for the manufacture of chloroacetaldehyde dimethyl acetal in which low-boiling constituents are distilled off completely or partially from the reaction mixture obtained by the reaction of vinyl acetate and chlorine in stoichiometric amounts in the presence of excess methanol, when the addition of chlorine is complete. The remaining liquid residue is neutralized with solid substances, such as oxides or carbonates of calcium and magnesium, while maintaining a temperature of from 20° to 60° C., until the aqueous extract has a pH of greater than 5. When neutralization is complete, the reaction mixture is in the form of two separate liquid phases. Once the upper organic layer has been separated off, it is fractionally distilled, pure chloroacetaldehyde dimethyl acetal being obtained as the main fraction yields of more than 90%, calculated on the vinyl acetate used.

5 Claims, No Drawings

PROCESS FOR THE MANUFACTURE OF CHLOROACETALDEHYDE DIMETHYL ACETAL

The invention relates to an improved process for the manufacture of chloroacetaldehyde dimethyl acetal by reacting vinyl acetate and chlorine in methanolic solution.

It is known to manufacture chloroacetaldehyde acetals by chlorinating vinyl compounds in alcoholic medium (see Ullmann, *Enzyklopadie der technischen Chemie*, 4th edition 1975, volume 9, page 375). When vinyl chloride is used, however, considerable amounts of 1,1,2-trichloroethane are formed as a byproduct (see U.S. Pat. No. 2,803,668), which, because of its similar boiling point, is difficult to separate from the chloroacetaldehyde dimethyl acetal.

This process can also be carried out with the addition of acid-binding reagents selected from the hydroxides, oxides, carbonates and alcoholates of metals of Groups Ia and IIa of the Periodic Table, as a result of which the equilibrium of the reaction should be shifted in favor of the desired acetal compound, and the 1,1,2-trichloroethane converted into 1,1-dichloroethylene (see DE-OS Nos. 16 43 899 and 16 93 017, which correspond to U.S. Pat. No. 3,784,612). However, the implementation of such processes of an industrial scale always involves expensive safety measures for the highly toxic vinyl chloride.

When a vinyl ether is used, it is necessary for alkaline agents, such as alkali metal or alkaline earth metal oxides, hydroxides, alcoholates, carbonates and bicarbonates, to be present during chlorination itself, in order to obtain the given yields (see U.S. Pat. No. 2,550,637), calcium oxide having proved especially suitable because of its limited solubility in methanol (see U.S. Pat. No. 3,379,772). It is, however, uneconomical to carry out these processes on an industrial scale as the starting compounds are not readily available, temperatures of below 0° C. are required in carrying out the process, and the yields of the desired acetal are low.

The reaction of vinyl acetate and a halogen in the presence of excess alcohol has also been known for a long time (see U.S. Pat. Nos. 2,330,570 and 2,411,826, and *Am. Chem. Soc., Vol.* 61, (1939), pages 1705–1706 by E. M. Filachione). The acetals were isolated from the reaction mixture by customary methods, for example, by the addition of water and by subsequent extraction of the acetal layer with a water-immiscible solvent, such as ether, chloroform or benzene. The organic extract was washed with water and/or an aqueous alkaline solution, such as a sodium bicarbonate solution, in order to remove acid or other water-soluble byproducts; the organic solvent was then distilled off and the acetal was purified by distillation. It has already been found by E. M. Filachione, however, that the yields of methyl haloacetals thus obtained are only approximately from 46% to 53% and are thus considerably lower than those of the corresponding ethyl haloacetals. This laborious working-up method is, however, uneconomical for manufacturing chloroacetaldehyde dimethyl acetal on an industrial scale, by this method, based on the readily available and non-toxic vinyl acetate, not only because of the poor yields that are achieved, but also from a technical point of view, as large amounts of solvent have to be distilled and recovery of the methanol from the aqueous phase requires additional expense.

The object of the invention is thus to provide an improved process for the manufacture of chloroacetaldehyde dimethyl acetal by reacting vinyl acetate and chlorine in stoichiometric amounts in the presence of excess methanol at temperatures of less than 20° C., while permitting the desired compound to be obtained in high yields and permitting the reaction mixture to be worked up without the addition of water and water-immiscible organic solvents.

This object is achieved according to the invention is that low-boiling constituents having boiling points of up to 60° C. are distilled off, completely or partially, from the reaction mixture when the addition of chlorine is complete, under the pressure of the surrounding atmosphere, by which a pressure of approximately 0.1 MPa is to be understood, the liquid residue is neutralized with solid substances selected from the group consisting of the oxides and carbonates of metals of the Group IIa of the Periodic Table while maintaining a temperature of from 20° C. to 60° C., the organic upper layer is separated off after phase separation is complete, and the resulting crude product is purified by distillation.

In carrying out the process of the invention, stoichiometric amounts of vinyl acetate and chlorine are advantageously introduced simultaneously into methanol, which has already been introduced initially, approximately 4 to 6 moles of methanol being used per mole of vinyl acetate, and it being ensured by adequate cooling, vigorous agitation and regulation of the rate of addition, that the reaction temperature does not exceed 20° C. Reaction temperatures in the range of from 0° to 10° C. are preferred. Once the addition of chlorine is complete, the reaction mixture is worked up under the conditions defined above, which are explained individually in more detail as follows.

Most of the hydrogen chloride formed as a byproduct is removed by distilling off the low-boiling constituents and, hence, the adverse effect of the hydrogen chloride on the chloroacetaldehyde dimethyl acetal, which is sensitive in the acid range, is cancelled. At the same time, approximately two-thirds, i.e., approximately 50–80% by weight, of the methyl acetate formed as a byproduct is removed and forms, with the methanol and in a weight ratio of 80/20, an azeotropic mixture boiling at 55° C., and, as a result, the reaction equilibrium likewise shifts in favor of the desired compound.

The solid substances of the type defined, oxides and carbonates of calcium and magnesium having proved especially suitable because of their ready availability, are added to the liquid residue remaining after the low-boiling constituents have been distilled off, immediately after that distillation operation. The solid substances can be used in the form of powders or granulates, the particle size of which is not important. In order to obtain a rapid reaction, however, the solid substances advantageously have particle sizes not exceeding 0.5 mm and their distribution in the liquid residue is advantageously ensured by vigorous agitation, for example by stirring. The amounts of the solid substances used are calculated such that they are sufficient to neutralize the liquid residue, that is to say, such that an aqueous extract thereof has a pH of greater than 5. The rate at which the solid substances are added is controlled as a function of the available cooling surface, such that the given temperature range, which is preferably from 30° to 50° C., is maintained.

When neutralization is complete, the reaction mixture is in the form of two separate liquid phases, the lower layer containing mainly the calcium chloride formed during neutralization, dissolved in methanol, and the upper, organic layer containing most of the crude chloroacetaldehyde dimethyl acetal. When the two phases have been separated in customary manner, the lower layer can, optionally, be extracted with methyl acetate.

The upper layer, optionally together with the methyl acetate extract from the lower layer, is then fractionally distilled, pure chloroacetaldehyde dimethyl acetal being obtained, as the main fraction, in yields of greter than 90%, calculated on the vinyl acetate used; chloroacetaldehyde dimethyl acetal is a valuable intermediate in the manufacture of perfumes, medicaments and plant protection agents.

The process of the invention is explained in more detail by means of the following example which is given by way of illustration, and not of limitation.

EXAMPLE 186 ml (172 g=2.0 moles) of vinyl acetate and 142 g (2.0) moles of chlorine were introduced simultaneously, over a period of one hour, into 324 ml of methanol with stirring and cooling, at from 0° to 2° C. 50 ml of low-boiling constituents were then distilled off using a 50 cm Vigreux column, 19.8 g of the middle runnings of a batch passed through in the same manner were then added and, finally, 34 g of calcium oxide were introduced over a period of 30 minutes, with stirring and cooling at 40° to 50° C. When neutralization was complete, the reaction mixture was in the form of two separate liquid phases. When the layers had been separated, the resulting upper layer was fractionated to yield 88 g of first runnings containing mainly methyl acetate and methanol, 19.8 g of middle runnings containing mainly methanol, chloroacetaldehyde and chloroacetaldehyde monomethyl and dimethyl acetals, and, as the main fraction, 223.1 g of chloroacetaldehyde dimethyl acetal, that is to say, 89.5% of the theoretical yield. If the lower layer formed after the addition of calcium oxide is then extracted twice by shaking with 100 ml of methyl acetate each time and the combined organic phases are distilled, 92.1% of the theoretical yield of chloroacetaldehyde dimethyl acetal is obtained.

While only one example of the present invention has been shown and described, it is obvious that many changes and modifications may be made thereunto without departing from the spirit and scope of the invention.

What is claimed is:

1. In a process for the manufacture of chloroacetaldehyde dimethyl acetal including the steps of reacting vinyl acetate and chlorine in stoichiometric amounts in the presence of excess methanol at temperatures of less than 20° C., and subsequently separating off the chloroacetaldehyde dimethyl acetal from the reaction mixture, the improvement comprising the steps of:

distilling off at least partially the low-boiling constituents having boiling points of up to 60° C. from the reaction mixture when the addition of chlorine is complete, under the pressure of the surrounding atmosphere, thereby producing a liquid residue;

neutralizing the liquid residue with solid substances selected from the group consisting of the oxides and carbonates of metals of Group IIa of the Periodic Table and a combination thereof, while maintaining a temperature of from 20° to 60° C., so as to produce a phase separation with an organic upper layer;

separating off the organic upper layer after phase separation is complete, to produce a crude product; and purifying the crude product by distillation to produce relatively pure chloroacetaldehyde dimethyl acetal.

2. The process of claim 1, wherein said low-boiling constituents are distilled off completely.

3. The process of claim 1, wherein said solid substances have a particle size not exceeding 0.5 mm.

4. The process of claim 1, wherein, during said neutralizing step, said residue is maintained at a temperature from 30° to 50° C.

5. The process of claim 1, wherein said solid substances are selected from the group consisting of oxides and carbonates of calcium and magnesium and a combination thereof.

* * * * *